United States Patent [19]
Kensey et al.

[11] Patent Number: 5,380,275
[45] Date of Patent: Jan. 10, 1995

[54] DEVICE FOR IRRIGATING A NATURAL BODY ORIFICE OF A PERSON SEATED ON A TOILET

[75] Inventors: Kenneth Kensey, Chester Springs; Joseph Kaufmann, Philadelphia, both of Pa.

[73] Assignee: Kensey Nash Corporation, Exton, Pa.

[21] Appl. No.: 52,319

[22] Filed: Apr. 23, 1993

[51] Int. Cl.⁶ ............................................. A61M 1/00
[52] U.S. Cl. ..................................... 604/27; 4/420.1; 604/275; 604/279
[58] Field of Search ................. 4/420.1; 604/213, 275, 604/257–262, 27, 279

[56] References Cited

U.S. PATENT DOCUMENTS

| | | | |
|---|---|---|---|
| 3,995,326 | 12/1976 | Umann | 4/420.1 |
| 4,000,742 | 1/1977 | DiGlacomo | 4/420.1 |
| 4,200,097 | 4/1980 | Hobbs, Jr. et al. | 604/213 |
| 4,504,270 | 3/1985 | Miller | 604/275 |
| 4,638,514 | 1/1987 | Landsberger | 4/420.1 |
| 5,250,024 | 10/1993 | Kensey | 604/257 |

Primary Examiner—Randall L. Green
Assistant Examiner—Rob Clarke
Attorney, Agent, or Firm—Caesar, Rivise, Bernstein, Cohen & Pokotilow, Ltd.

[57] ABSTRACT

A device for administering a liquid into the body of a person through a natural orifice, e.g., the anus or vagina, while the person is seated on a toilet. The device comprises a base unit, an extendable tube having a distal end, and a vessel containing the liquid for introduction into person. The base unit comprises a saddle arranged for disposition under the toilet seat and configured to be disposed between the buttocks of the person when he/she is seated the seat. A positionable guide tube extends through a portion of the saddle from an entrance point adjacent the front of the toilet to an opening located at a position adjacent the natural orifice, e.g., anus or vagina, when the person is seated. The extendable tube has a distal end portion arranged to be inserted by the person into the guide tube and through the opening, and the guide tube is arranged to be slid with respect to the saddle, so that the distal end portion of the extendable tube is directed upward and enters the natural orifice. The vessel is coupled to the extendable tube by a pump and associated connector so that the liquid within the vessel can be pumped through the extendable tube into the person's body.

16 Claims, 3 Drawing Sheets

DEVICE FOR IRRIGATING A NATURAL BODY ORIFICE OF A PERSON SEATED ON A TOILET

BACKGROUND OF THE INVENTION

This invention relates generally to medical devices and more particularly to devices which are suitable for use by a lay person to readily self-administer any type of irrigation or therapeutic agent into the person's anus or vagina while that person is seated on a toilet.

One common problem with aged or infirm persons is the tendency to have fecal impactions, thereby necessitating an enema or some other similar procedure for relief. Prior art devices for providing an enema or otherwise irrigating the person's bowel leave much to be desired from the standpoint of ease of use. In this regard prior art devices tend to be generally somewhat difficult to insert through the anus by the aged or infirm.

In copending U.S. patent application, Ser. No. 934,378 filed on Aug. 24, 1992, entitled System For Introducing A Therapeutic Agent Into The Rectum, which is assigned to the same assignee as this invention and whose disclosure is incorporated by reference herein there is disclosed a system and method which overcomes much of the disadvantages of the prior art. Specifically that system basically comprises a device for administering a liquid into the bowel of a person through the person's anus. The device includes an introducer and an associated manually actuatable pump and reservoir. The introducer comprises a relatively rigid hollow conduit, e.g., a J-shaped tube, having a curved distal section and an elongated proximal section. The curved distal section terminates at a free end in the form of a tip configured for ready passage into the anus. The elongated section of the conduit has a proximal end and is sufficiently long that when the person is seated on a toilet with the proximal end located between the person's legs adjacent the person's thighs the tip is located at the person's anus. Thus, the person can readily insert the tip into the anus by manually manipulating the proximal section of the conduit. The free end of the conduit has at least one aperture therein. The pump is coupled to the proximal section of the conduit and is arranged to be operated by the person to pump a liquid through the conduit from the reservoir and out the apertures in the distal end into the person's bowel.

While the device of the above mentioned patent application is generally suitable for its intended purposes, it never the less still leaves something to be desired from the standpoint of ease of use, particularly by aged or infirm persons. Thus, a need exists for a device which is very easy to use. Moreover, a need exists for a device which can be readily used to effect the irrigation of the vagina.

OBJECTS OF THE INVENTION

Accordingly, it is a general object of this invention to provide a system which addresses those needs.

It is a further object of this invention to provide a device for use by a person seated on a toilet to self-administer an enema or otherwise irrigate his/her bowel.

It is still a further object of this invention to provide a device for use by a person seated on a toilet to self-irrigate her vagina.

It is yet further object of this invention to provide a device which is simple in construction and easy to use to effect the introduction of a liquid into a natural orifice of a person by the person while seated on a toilet.

SUMMARY OF THE INVENTION

These and other objects of this invention are achieved by providing a device for administering a material, e.g., a liquid, into an internal portion, e.g., the bowel, of a person through a natural orifice, e.g., the anus, while the person is seated, e.g. sitting on a toilet having a seat. The device basically comprising a base unit, and extendable tube means. The base unit is arranged for disposition under the toilet seat and comprises saddle means configured to be located in a space adjacent the buttocks of a person seated on that seat, and passageway means extending through a portion of the saddle means and having an opening therein. The passageway means is positionable so that the opening is located at a position adjacent the natural orifice, e.g., the anus, of the person when that person is seated on the toilet seat.

The extendable tube means has a distal end portion arranged to be inserted into the passageway and through the opening so that the distal end portion of the tube means enters the natural orifice of the person to carry the material, e.g., the liquid, into the person's body through that orifice.

In accordance with one preferred embodiment of the invention the material introduced into the patient's body is provided from fluid supply means. That means is arranged to be coupled to the extendable tube means to provide, e.g., pump, the fluid, e.g., a liquid, through the extendable tube means into the internal portion, e.g., the rectum, of the person.

BRIEF DESCRIPTION OF THE DRAWING

Other objects and many of the attendant advantages of this invention will be readily appreciated as the same becomes better understood by reference to the following detailed description when considered in connection with the accompanying drawings wherein.

DETAILED DESCRIPTION OF THE PREFERRED EMBODIMENT

Figure 1:
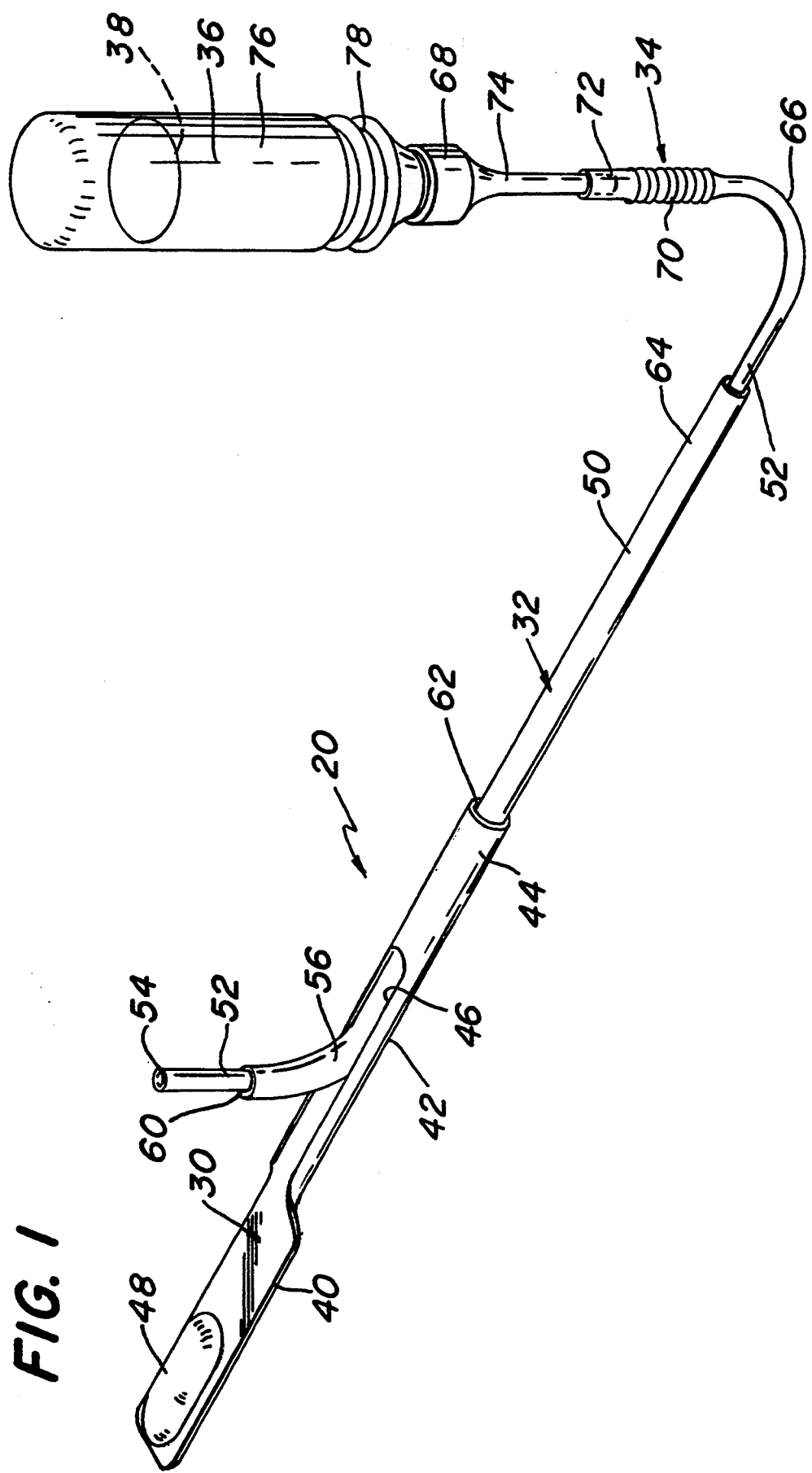
FIG. 1 is an isometric view of a device constructed in accordance with this invention.
Figure 4:
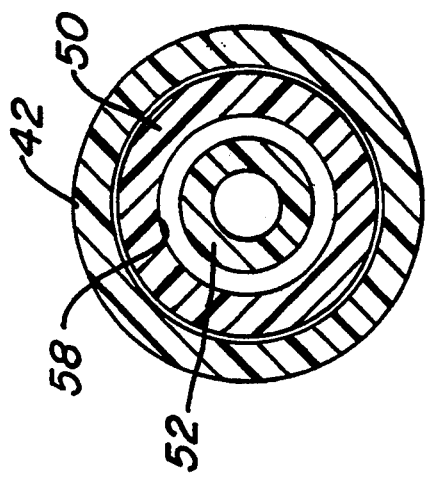
FIG. 4 is an enlarged sectional view taken along line 4—4 of FIG. 3.
Figure 5:
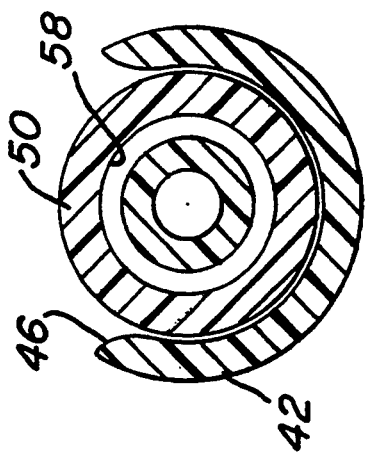
FIG. 5 is an enlarged sectional view taken along line 5—5 of FIG. 3.

Referring now in greater detail to the figures there is shown at 20 in FIG. 1 one embodiment of a device constructed in accordance with this invention. The device 20 is arranged to be mounted, e.g., disposed, on the rim 22A (FIG. 2) of the bowl of a conventional toilet 22 under the seat 24 to enable a person 26 to sit on the seat so that he/she can manipulate the device to introduce a portion of it into the anus 28 to effect the self-administration of an irrigation and/or therapeutic liquid into the rectum or bowel. The device can also be used for the self-administration of an irrigation and/or therapeutic liquid into the vagina (also denoted by the reference number 28 in FIG. 2). Thus, depending upon the application desired any type of liquid irrigation and/or therapeutic agent, such as soapy water, salt water, oils (mineral or vegetable), may be used by the device 20.

As can be seen in FIG. 1 the device 20 basically comprises a base unit 30, an extendable tube assembly 32, and pump/liquid supply assembly 34. The pump/liquid supply assembly 34 is arranged to be releasably connected to a supply vessel or bottle 36 containing some irrigation and/or therapeutic liquid 38 therein. The base unit 30 basically comprises an elongated tubular member formed as an integral unit of any suitable material, e.g., a rigid plastic or cardboard. The unit has a rear section in the form of a flange or plate 40, a tubular intermediate section 42, and a tubular front section 44. The intermediate tubular section 42 includes an elongated slot 46 extending a substantially distance along the top surface of the section 42 parallel to the longitudinal axis of base unit. The slot 46 serves to receive a portion of the extendable tube assembly 32 to orient that assembly in a desired direction (as will be described later). The section 42 will be hereinafter referred to as the "saddle" of the base unit, for reasons which will become apparent later.

In accordance with a preferred embodiment of this invention the base unit 30 is not fixedly secured to the toilet but is releasably secured thereto, so that the device 20 can be readily removed from the toilet for cleaning or disposal, when desired. To achieve the releasable securement frictional means are provided to frictionally hold the base unit in place. That means basically comprises an elongated, resilient material, e.g., silicone rubber, pad or cushion 48 secured by any suitable means, e.g., an adhesive, to the top surface of the plate 40. The pad 48 is of a sufficient thickness so that when the base unit 30 is in place, like shown in FIG. 2, the undersurface 24A of the rear of the toilet seat 24 tightly engages the top surface of the pad 48, while the underside of the plate 40 rests on the top surface of the bowl's rim 22A. Thus, when the user 26 is seated on the toilet seat, the base unit 30 is tightly interposed between the undersurface of the toilet seat and the top surface of the rim of the toilet bowl so that the device 20 is held in place by friction.

The base unit 30 is designed to be centered over the toilet bowl and oriented so that it extends from the rear of the bowl toward the front of the bowl. In particular, the free end of the front portion 44 of the base unit 30 terminates closely adjacent the front rim of the toilet bowl. A portion of the extendable tube assembly 32 (to be described shortly hereafter) extends through the tubular portion of the base unit 30 and projects outward beyond the free end of the front portion 44 of the base unit. This portion of the extendable tube assembly also extends over and rests on the top surface of the front rim of the toilet bowl. In such an arrangement the elongated intermediate saddle portion 42 of the base unit 30 is generally centered and spans over the bowl between the front and the back thereof.

As can be seen clearly in FIGS. 3-6, the extendable tube assembly 32 basically comprises a guide member 50 and a liquid conveying conduit 52. The guide member 50 serves to receive the conduit 52 therein and to guide the distal free end 54 of the conduit into the anus (or vagina) of the user, as will be described later. The guide member 50 is a tube formed of any suitable rigid material, e.g., a plastic or cardboard, and is linear except for its distal end section 56, which is arcuate. A central passageway 58 extends through the entire length of the tubular guide member 50 so that its distal end 60 is open, as is its proximal end 62. The guide member 50 is arranged to be received in the base unit 30 for longitudinal movement therealong. In particular, the guide member 50 is located within the tubular portion of the base unit 30 so that the arcuate end section 56 of the guide member is located within the slot 46, while its linear section extends through the base unit's saddle 42 and front section 44 so that the proximal end portion 64 of the guide member 50 extends out of the open end 62 of the base unit, as shown clearly in FIG. 2.

As mentioned earlier a portion of the extendable tube assembly 32 rests on the top surface of the front rim of the toilet bowl and extends beyond that rim. That portion constitutes the proximal end portion 64 of the guide member and serves as a "handle" for the device 20.

The liquid carrying conduit 52 is formed of any suitable flexible, liquid-proof material, e.g., a firm silicone elastomer, and is extended through the guide member 50 so that its open free distal end 54 projects out of the open end 60 of the guide member 50. The front or proximal portion 66 of the conduit 52 extends out of the handle section 64 and is connected to and in fluid communication with the pump/liquid supply assembly 34.

The internal diameter of the passageway 58 through the guide member is slightly larger than the external diameter of the conduit 52, so that the conduit 52 can be slid therethrough to a desired longitudinal position, i.e., so that its open distal end 54 projects beyond the open distal end 60 of the guide tube, but is in sufficient frictional engagement therewith that it is resistant to movement with respect to the guide tube once it is in the desired position. Accordingly, the longitudinal movement of the guide tube by the user of the device, as will be described later, effects the corresponding movement of the conduit 52.

Figure 2:
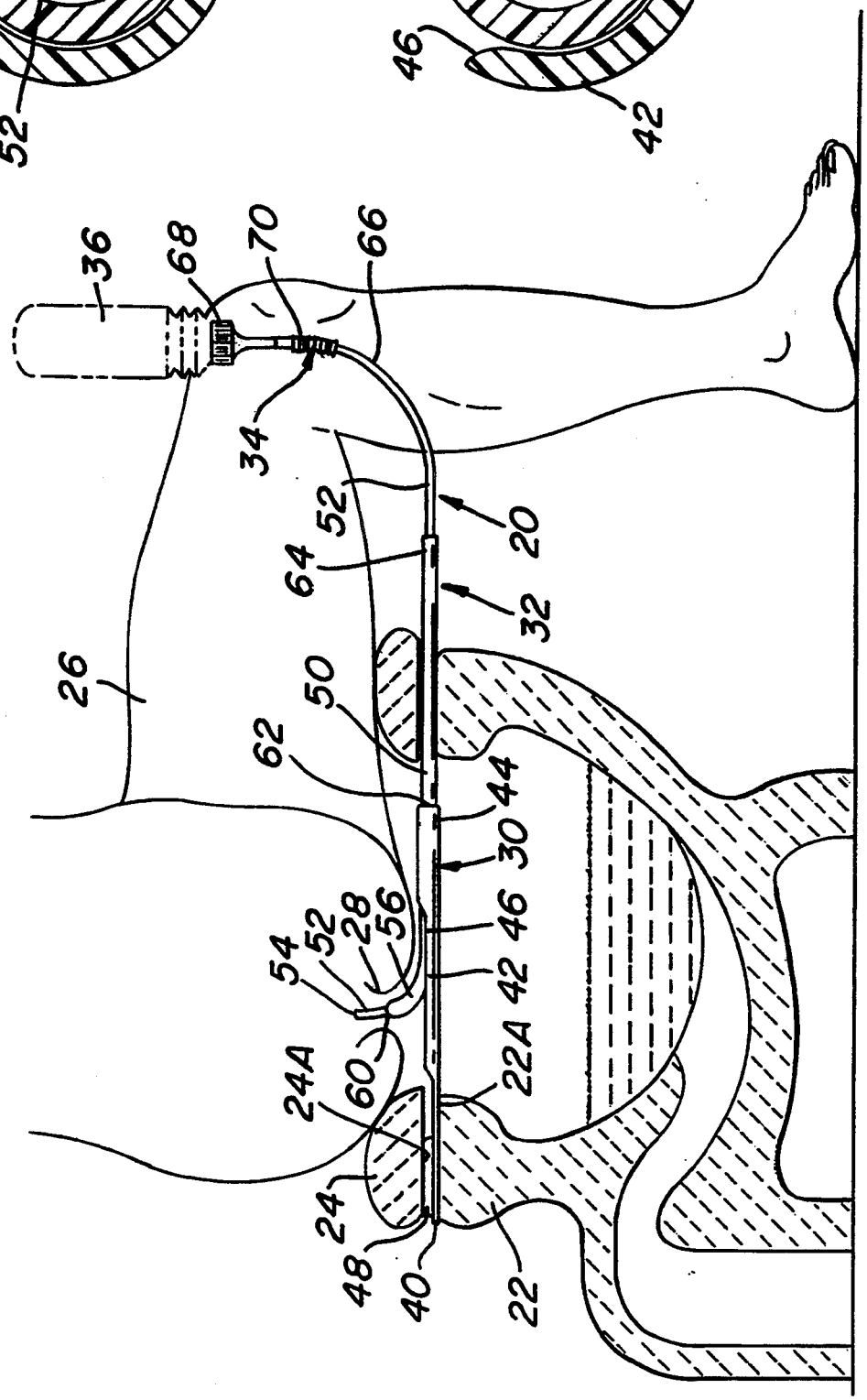
FIG. 2 is a side elevational view, partially, in section showing the device of FIG. 1 in one typical use, e.g., to introduce a liquid into the rectum of a person.
Figure 3:
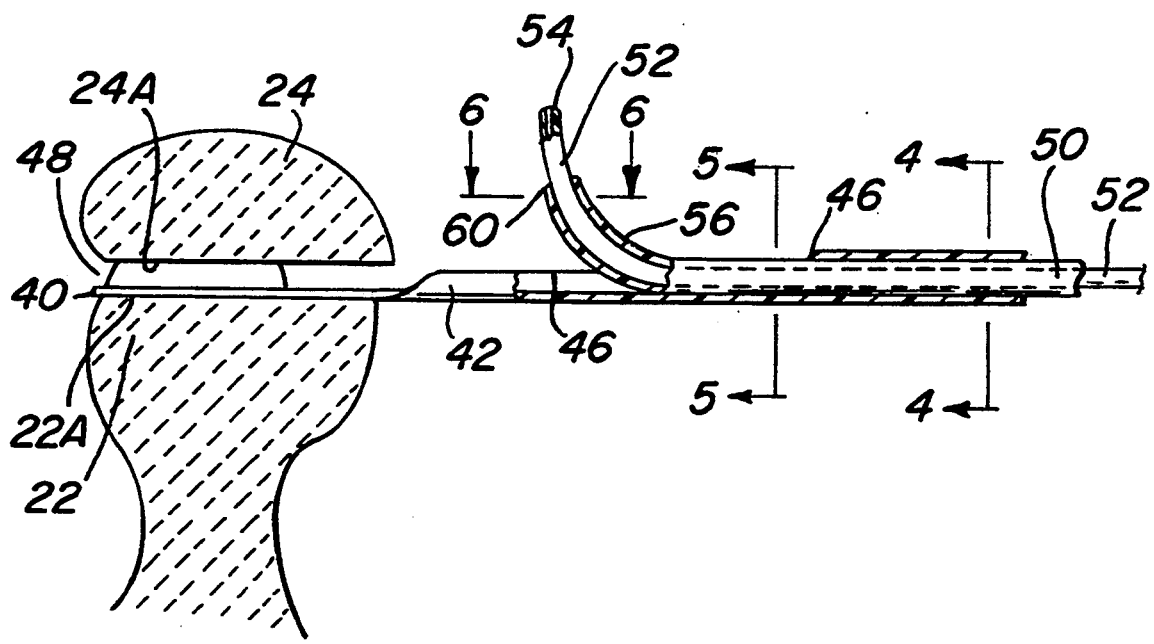
FIG. 3 is an enlarged side elevational view, partially in section, showing a portion of the device shown in FIG. 2.
Figure 6:
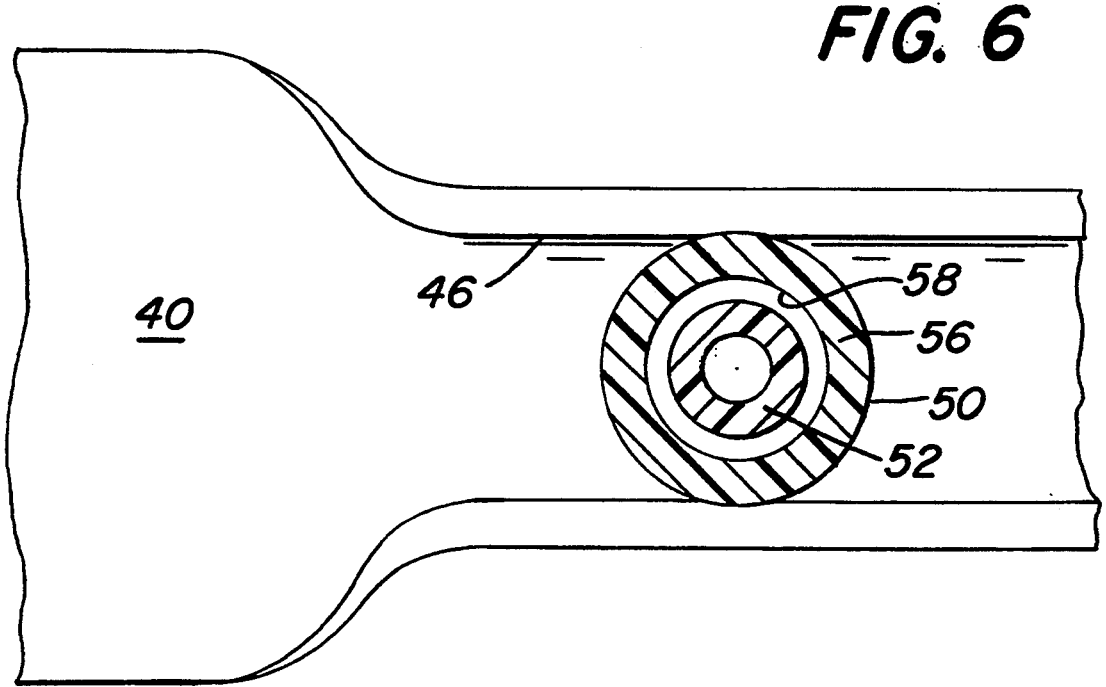
FIG. 6 is an enlarged sectional view taken along line 6—6 of FIG. 3.

A can be seen clearly in FIGS. 1-3 when the arcuate end section 56 of the guide tube 50 is located within the slot 46 of the base unit 30, the open free end 60 of that arcuate section will be directed generally upward. When the device 20 is in place on the toilet 22 and the user 26 of the device is seated on the toilet seat 24 the saddle portion 42 of the device is located underneath the space between the user's buttocks. The guide tube 50 is arranged to be slid within the base unit 30 to the "operative" longitudinal position wherein the open free end 60 of the guide member 50 is disposed under the anus or vagina of the user. This is accomplished by the user of the device grasping the handle section 64 of the guide member and either sliding it forward or backward as required. When the free end 54 of the conduit is immediately adjacent, and preferably slightly forward of the anus or vagina, as the case may be, the person can then slide the guide member 50 slightly to the rear to cause the free end 54 to enter the anus or vagina. Entry of the free end 54 of the conduit 52 into the anus or vagina can be expedited by the user grasping the portion of the conduit 52 extending beyond the open end 62 of the guide member to slide the conduit to the rear with respect to the guide member.

The distal end 54 or tip of the conduit 52 is designed so that it can, without trauma, readily enter the anus or vagina when directed thereto and a modest force applied. To that end the material making up conduit 50, e.g., a firm silicone elastomer, is resistant to longitudinal collapse. Moreover, its tip is somewhat rounded. One particularly effective shape for the tip is that of the COMFORTIP TM tip used on the disposable squeeze bottle of the enema product sold by C.B. Fleet Company, Inc., of Lynchburg VA under the registered trademark FLEET.

Once the open end or tip 54 of the liquid carrying conduit 52 has passed through the natural body opening to the desired position within the user's body, e.g., through the anus and into the rectum, the device 20 is ready to be used to introduce the liquid 38. As mentioned earlier that liquid is held within the bottle or vessel 36.

In accordance with one preferred aspect of this invention the pump/supply assembly 34 includes a threaded cap 68 for connection to various, self-contained or bottled commercial enemas or douches. Thus, when the device 20 is used for giving an enema, a conventional bottled enema product, such as that sold under the registered trademark NATURE'S REMEDY by SmithKline Beecham, and which is contained within the bottle designated by the registered trademark FLEX-NECK, may be used with it. That product basically comprises a liquid contained within bottle 36 having a cylindrical body 76 and a corrugated end 78 terminating in a threaded mouth (not shown). When that product is to be used with device 20 the threaded mouth of the bottle 36 is screwed within the threaded cap 68 of the pump/supply assembly 34. Other conventional bottled enema or douche products may be used with the device 20.

Turning now to FIGS. 1 and 2 it can be seen that the pump/supply assembly 34 basically comprises the heretofore identified threaded cap 68, as well as a manually operable pump 70. The pump itself comprises a hollow cylindrical member having a corrugated sidewall formed at the proximal end of the supply conduit 52. The pump includes an inlet port in the form of a tube 72 which is in fluid communication with the hollow interior of the corrugated sidewall. The cap 68 of the pump/supply assembly includes a rigid tube 72 which is to be arranged to be extended into the pump's inlet tube 72.

The pump 68 is arranged to be manually squeezed to collapse it longitudinally, and thereby force the liquid 28 provided to its interior out of it and into the conduit 52 for passage into the rectum or vagina of the user. Other types of pumps for pumping the liquid 38 from into conduit 52 can be utilized, if desired.

In order to facilitate the tip 54 insertion procedure, the rear plate 40 of the base unit 30 is of a sufficient width so that when it is interposed between the toilet seat 24 and the toilet rim 24 the base unit 30 will be prevented from twisting about its longitudinal axis as the user 26 sits on the device. This action ensures that the outlet opening 60 of the guide tube will be held in the position wherein it is directed upward toward the anus or vagina to ensure that the supply conduit's tip 54 will enter easily and without trauma.

As should be appreciated from the foregoing the device of this invention allows the self administration of a liquid agent into a natural body orifice while the person is seated on the toilet. When used in vaginal applications, e.g., douching, the guide conduit is slid forward slightly with respect to the base unit to align its outlet opening 60 with the vagina. When used in rectal applications the guide tube is slid backward slightly with respect to the base unit to align the outlet with the anus.

Irrespective of the application, the subject invention provides aged or infirm persons, or others with limited flexibility, with a viable means for gaining access to the rectum or vagina without contortion. While the device of this invention is arranged to enable the self-administration of the irrigation and/or therapeutic liquid, it is of course apparent that it may be used on a person by an aide if the person is incapable or does not desire to use the device on himself/herself.

Without further elaboration the foregoing will so fully illustrate our invention that others may, by applying current or future knowledge, adopt the same for use under various conditions of service.

We claim:

1. A device for administering a material into a natural orifice of a person while said person sits on a toilet having a conventional bowl with a conventional toilet seat disposed thereover to form a space therebetween, said device comprising a base unit, and extendable tube means, said base unit being arranged for releasable disposition within said space on said bowl and under said toilet seat to be held by friction therebetween, said base unit comprising elongated saddle means configured to be disposed in a space between the buttocks of a person seated on said toilet seat, and passageway means extending longitudinally through a portion of said elongated saddle means, said passageway means having an opening therein and being slidable longitudinally through said portion of said elongated saddle means so that said opening is located at a position adjacent said natural orifice when said person is seated on said toilet seat, said extendable tube means having a distal end portion slidably mounted within said passageway means so that it can be slid longitudinally therethrough, whereupon said distal end portion is located outside said opening to enter said natural orifice to carry said material into the body of said person through said natural orifice.

2. The device of claim 1 wherein said material comprises a liquid, and wherein said system additionally comprises liquid supply means, said liquid supply means being connectable to said extendable tube means to provide a said liquid through said extendable tube means into the body of said person through said natural orifice.

3. The device of claim 1 wherein said distal end portion of said extendable tube means is in the form of a tip configured for ready passage into said natural orifice.

4. The device of claim 2 wherein said liquid supply means comprises pumping means connected to said extendable tube means and a vessel arranged to be releasably secured to said pumping means.

5. The device of claim 1 wherein said toilet seat comprises a front and a rear, and wherein said passageway means comprises an elongated tubular member having one end at which said opening is located and which extends generally horizontally from said one end through said saddle means to an entrance point in said saddle means located adjacent said front of said toilet seat, and wherein said passageway means is configured to direct said distal end of said extendable tube means generally upward for passage through said opening and into said natural orifice of said person.

6. The device of claim 2 wherein said toilet seat comprises a front and a rear, and wherein said passageway means comprises an elongated tubular member having one end at which said opening is located and which extends generally horizontally from said one end through said saddle means to an entrance point in said saddle means located adjacent said front of said toilet seat, and wherein said passageway means is configured to direct said distal end of said extendable tube means generally upward for passage through said opening and into said natural orifice of said person.

7. The system of claim 6 wherein said liquid supply means additionally comprises pumping means and extendable tube for pumping said liquid.

8. The device of claim 7 wherein said pumping means is arranged to be operated manually.

9. The device of claim 8 wherein said pumping means comprises a cylindrical member having a corrugated sidewall arranged to be manually compressed longitudinally.

10. The device of claim 7 wherein said fluid supply means additionally comprises a vessel for holding said liquid and releasably securable coupling means for connecting said vessel to said pumping means.

11. The device of claim 2 wherein said extendable tube means comprises an elongated flexible member extending through and slidable with respect to said passageway means.

12. The device of claim 5 wherein said extendable tube means comprises an elongated flexible member extending through and slidable with respect to said passageway means.

13. The device of claim 6 wherein said extendable tube means comprises an elongated flexible member extending through and slidable with respect to said passageway means.

14. The device of claim 5 additionally comprising means for holding said device in place on said toilet.

15. The device of claim 14 wherein said means for holding comprises a plate arranged to be disposed on a surface of said toilet bowl under said toilet seat.

16. The device of claim 15 wherein said plate comprises a frictional engagement pad.

* * * * *